(12) United States Patent
Blatter et al.

(10) Patent No.: US 9,046,339 B2
(45) Date of Patent: Jun. 2, 2015

(54) SYSTEMS AND METHODS FOR BIDIRECTIONAL FUNCTIONAL OPTICAL COHERENCE TOMOGRAPHY

(71) Applicant: Carl Zeiss Meditec, Inc., Dublin, CA (US)

(72) Inventors: Cedric Blatter, Boston, MA (US); Rainer A. Leitgeb, Vienna (AT)

(73) Assignee: Carl Zeiss Meditec, Inc., Dublin, CA (US)

( * ) Notice: Subject to any disclaimer, the term of this patent is extended or adjusted under 35 U.S.C. 154(b) by 0 days.

(21) Appl. No.: 14/503,292

(22) Filed: Sep. 30, 2014

(65) Prior Publication Data

US 2015/0092195 A1 Apr. 2, 2015

Related U.S. Application Data

(60) Provisional application No. 61/884,419, filed on Sep. 30, 2013.

(51) Int. Cl.
*G01B 9/02* (2006.01)
*A61B 5/026* (2006.01)
*A61B 3/10* (2006.01)

(52) U.S. Cl.
CPC .......... *G01B 9/02091* (2013.01); *A61B 5/0261* (2013.01); *A61B 3/102* (2013.01)

(58) Field of Classification Search
CPC ...... G01B 9/02; A61B 5/0066; A61B 5/6852; A61B 5/0073; G01N 21/4795

USPC ........................................................ 356/479
See application file for complete search history.

(56) References Cited

U.S. PATENT DOCUMENTS

| 8,244,334 B2 | 8/2012 | Huang et al. |
| 8,433,393 B2 | 4/2013 | Sharma et al. |
| 2003/0208326 A1* | 11/2003 | Chen et al. ...................... 702/49 |
| 2008/0025570 A1* | 1/2008 | Fingler et al. ................. 382/107 |
| 2013/0301000 A1 | 11/2013 | Sharma et al. |

OTHER PUBLICATIONS

An et al., "Ultrahigh Sensitive Optical Microangiography for in vivo Imaging of Microcirculations within Human Skin Tissue Beds", Optics Express, vol. 18, No. 8, Apr. 12, 2010, pp. 8220-8228.
Bachmann et al., "Resonant Doppler Flow Imaging and Optical Vivisection of Retinal Blood Vessels", Optics Express, vol. 15, No. 2, Jan. 2007, pp. 408-422.
Baumann et al., "Total Retinal Blood Flow Measurement With Ultrahigh Speed Swept Source/Fourier Domain OCT", Biomedical Optics Express, vol. 2, No. 6, Jun. 2011, pp. 1539-1552.

(Continued)

*Primary Examiner* — Tarifur Chowdhury
*Assistant Examiner* — Md Rahman
(74) *Attorney, Agent, or Firm* — Morrison & Foerster LLP

(57) ABSTRACT

Methods for determining improving quantitative and qualitative motion contrast information collected with optical coherence tomography (OCT) data are presented. In one embodiment, flow within a cross-sectional area of a sample is calculated independent of the Doppler and en face angles using a bidirectional OCT system. In another embodiment, motion contrast images are improved by averaging motion contrast information collected from a bidirectional OCT system.

15 Claims, 6 Drawing Sheets

(56) References Cited

OTHER PUBLICATIONS

Blatter et al., "Dove Prism Based Rotating Dual Beam Bidirectional Doppler OCT", Biomedical Optics Express, vol. 4, No. 7, Jul. 1, 2013, pp. 1188-1203.

Blatter et al., "Ultrahigh-Speed Non-Invasive Widefield Angiography", Journal of Biomedical Optics, vol. 17, No. 7, Jul. 2012, pp. 070505-1-070505-3.

Blatter et al., "Angle Independent Flow Assessment with Bidirectional Doppler Optical Coherence Tomography", Optics Letters, vol. 38, No. 21, Nov. 1, 2013, pp. 4433-4436.

Choi et al., "Measurement of Pulsatile Total Blood Flow in the Human and Rat Retina with Ultrahigh Speed Spectral/Fourier Domain Oct", Biomedical Optics Express, vol. 3, No. 5, May 1, 2012, pp. 1047-1061.

Fingler et al., "Mobility and Transverse Flow Visualization Using Phase Variance Contrast with Spectral Domain Optical Coherence Tomography", Optics Express, vol. 15, No. 20, Oct. 1, 2007, pp. 12636-12653.

Fingler et al., "Volumetric Microvascular Imaging of Human Retina using Optical Coherence Tomography with a Novel Motion Contrast Technique", Optics Express, vol. 17, No. 24, Nov. 23, 2009, pp. 22190-22200.

Iftimia et al., "Dual-Beam Fourier Domain Optical Doppler Tomography of Zebrafish", Optics Express, vol. 16, No. 18, Sep. 1, 2008, pp. 13624-13636.

Jia et al., "Split-Spectrum Amplitude-Decorrelation Angiography with Optical Coherence Tomography", Optics Express, vol. 20, No. 4, Feb. 13, 2012, pp. 4710-4725.

Leitgeb, Rainer A., "Current Technologies for High-Speed and Functional Imaging with Optical Coherence Tomography", Advances in Imaging and Electron Physics, vol. 168, Chapter 3, 2011, pp. 109-192.

Makita et al., "Quantitative Retinal-Blood Flow Measurement with Three-Dimensional Vessel Geometry Determination using Ultrahigh-Resolution Doppler Optical coherence Angiography", Optics Letters, vol. 33, No. 8, Apr. 15, 2008, pp. 836-838.

Mariampillai et al., "Optimized Speckle Variance OCT Imaging of Microvasculature", Optics Express, vol. 35, No. 8, Apr. 15, 2010, pp. 1257-1259.

Mariampillai et al., "Speckle Variance Detection of Microvasculature Using Swept-Source Optical Coherence Tomography", Optics Letters, vol. 33, No. 13, Jul. 1, 2008, pp. 1530-1532.

Michaely et al., "Vectorial Reconstruction of Retinal Blood Flow in three Dimensions Measured with High Resolution Resonant Doppler Fourier Domain Optical Coherence Tomography", Journal of Biomedical Optics, vol. 12, No. 4, Jul./Aug. 2007, pp. 041213-1-041213-7.

Pilch et al., "Automated Segmentation of Retinal Blood Vessels in Spectral Domain Optical Coherence Tomography Scans.", Biomedical Optics Express, vol. 3, No. 7, Jul. 2012, pp. 1478-1491.

Riva et al., "Bidirectional LDV System for Absolute Measurement of Blood Speed in Retinal Vessels", Applied Optics, vol. 18, No. 13, Jul. 1, 1979, pp. 2301-2306.

Schmoll et al., "Heart-Beat-Phase-Coherent Doppler Optical Coherence Tomography for Measuring Pulsatile Ocular Blood Flow", Journal of Biophotonics, vol. 6, No. 3, 2013, pp. 275-282.

Schmoll et al., "Ultra-High-Speed Volumetric Tomography of Human Retinal Blood Flow", Optics Express, vol. 17, No. 5, Mar. 2, 2009, pp. 4166-4176.

Singh et al., "Segmentation of Doppler Optical Coherence Tomography Signatures Using a Support-Vector Machine", Biomedical Optics Express, vol. 2, 2011, 12 pages.

Singh, et al., "Stable Absolute Flow Estimation with Doppler OCT based on Virtual Circumpapillary Scans", Biomedical Optics Express, vol. 1, No. 4, Nov. 1, 2010, pp. 1047-1059.

Sorzano et al., "Elastic Registration of Biological Images Using Vector-Spline Regularization", IEEE Transactions on Biomedical Engineering, vol. 52, No. 4, Apr. 2005, pp. 652-663.

Srinivasan et al., "Quantitative Cerebral Blood Flow with Optical Coherence Tomography", Optics Express, vol. 18, No. 3, Feb. 1, 2010, pp. 2477-2494.

Szkulmowski et al., "Phase-Resolved Doppler Optical Coherence Tomography-Limitations and Improvements", Optics Letters, vol. 33, No. 13, Jul. 1, 2008, pp. 1425-1427.

Szkulmowski et al., "Flow Velocity Estimation using Joint Spectral and Time Domain Optical Coherence Tomography", Optics Express, vol. 16, No. 9, Apr. 28, 2008, pp. 6008-6025.

Wang et al., "Retinal Blood Flow Measurement by Circumpapillary Fourier Domain Doppler Optical Coherence Tomography", J. Biomed. Opt., vol. 13, No. 6, 2008, 22 pages.

Wehbe et al., "Automatic Retinal Blood Flow Calculation using Spectral Domain Optical Coherence Tomography", Optics Express, vol. 15, No. 23, 2007, pp. 15193-15206.

Werkmeister et al., "Measurement of Absolute Blood Flow Velocity and Blood Flow in the Human Retina by Dual-Beam Bidirectional Doppler Fourier-Domain Optical Coherence Tomography", Investigative Ophthalmology & Visual Science, vol. 53, No. 10, Sep. 2012, pp. 6062-6071.

Werkmeister et al., "Bidirectional Doppler Fourier-Domain Optical Ccherence Tomography for Measurement of Absolute Flow Velocities in Human Retinal Vessels", Optics Letters, vol. 33, No. 24, Dec. 15, 2008, pp. 2967-2969.

\* cited by examiner

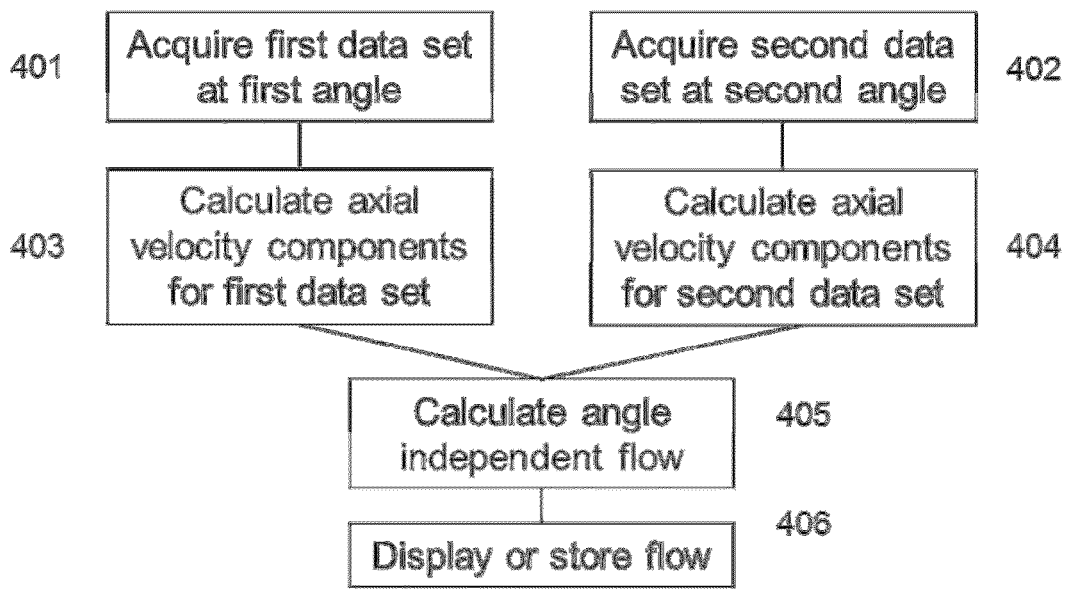
FIG. 4(a)
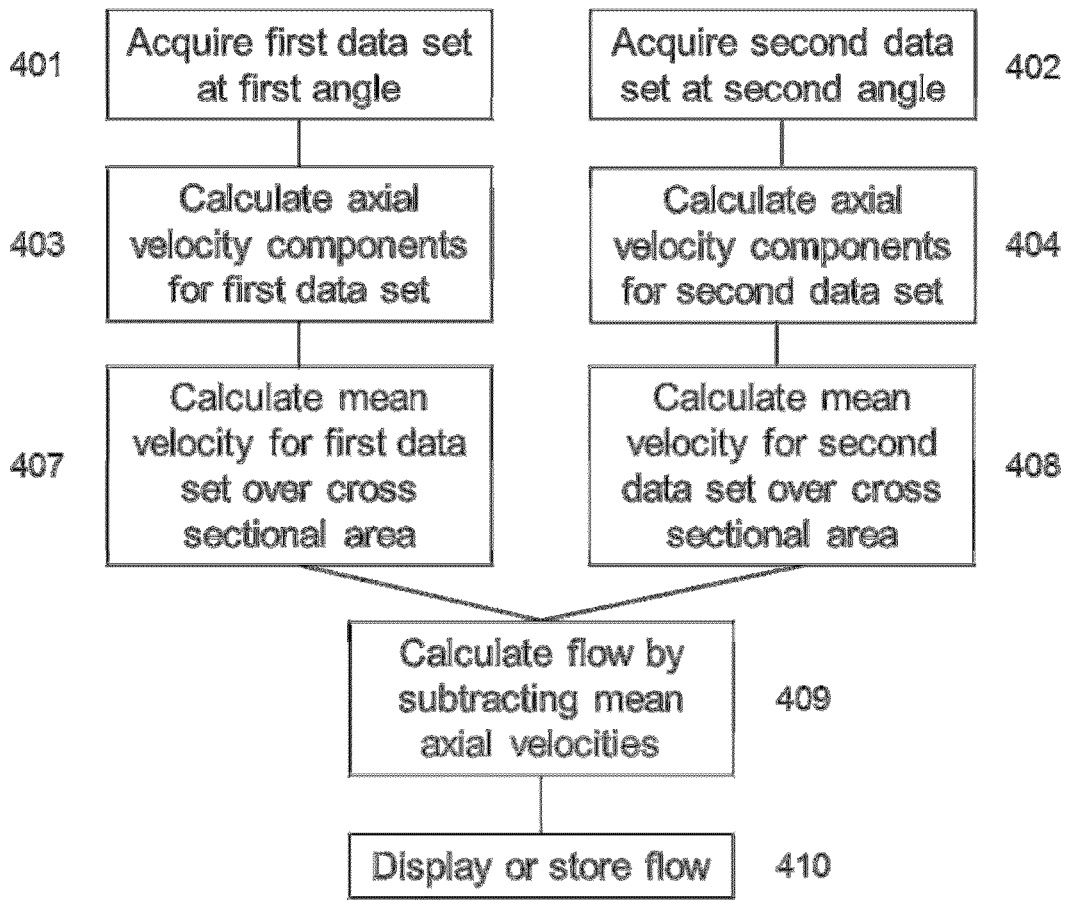
FIG. 4(b)
FIG. 4

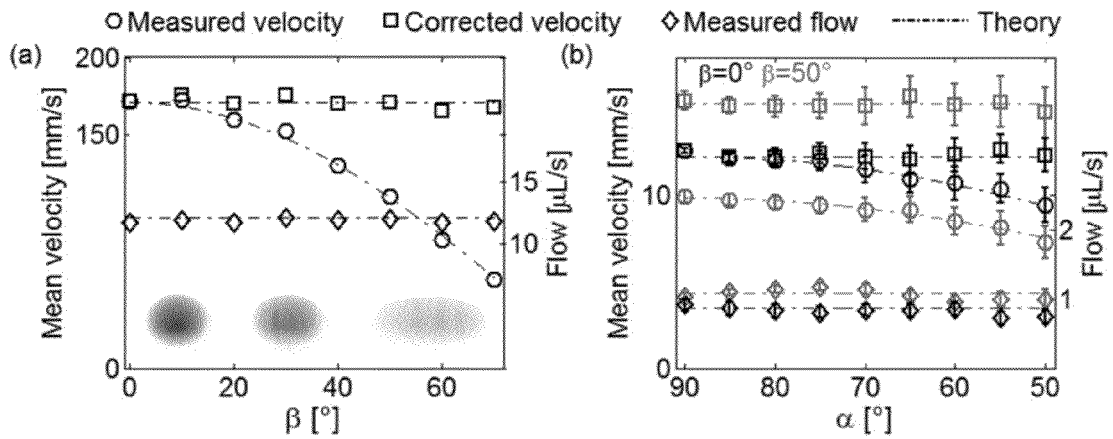
FIG. 5(a)　　FIG. 5(b)
FIG. 5
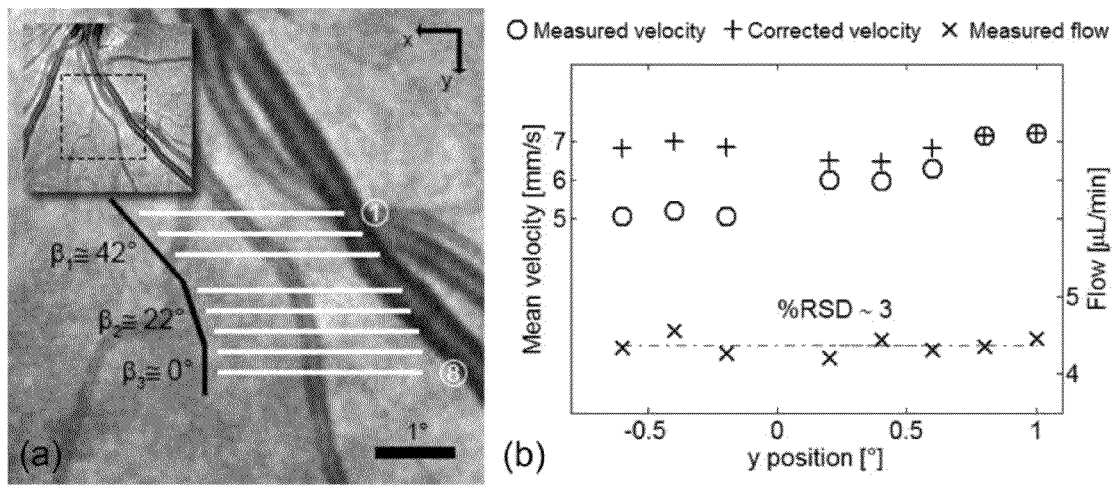
FIG. 6(a)　　FIG. 6(b)
FIG. 6

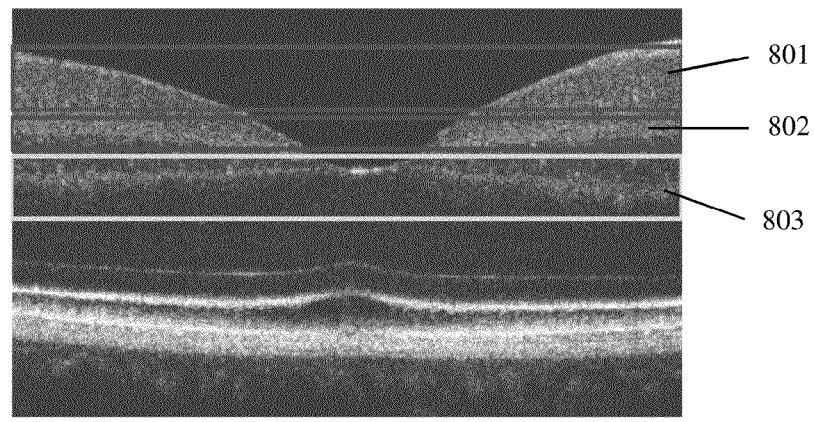
FIG. 8(a)
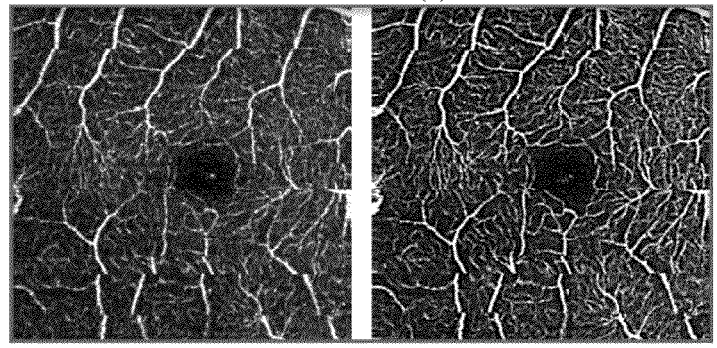
FIG. 8(b)
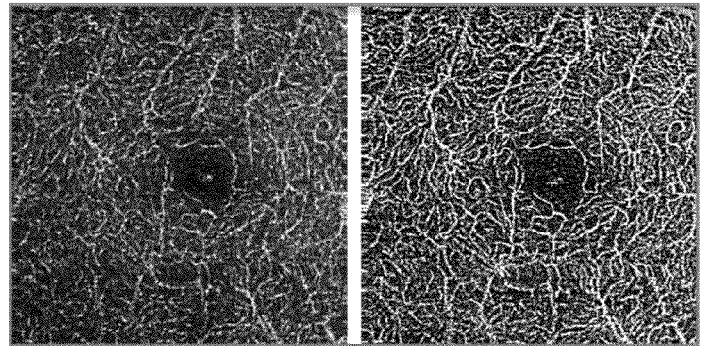
FIG. 8(c)
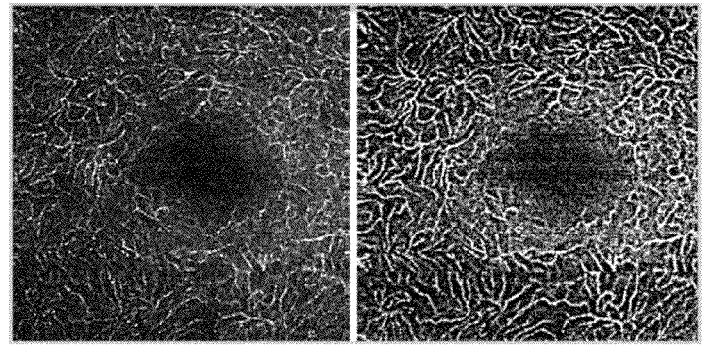
FIG. 8(d)
FIG. 8

SYSTEMS AND METHODS FOR BIDIRECTIONAL FUNCTIONAL OPTICAL COHERENCE TOMOGRAPHY

PRIORITY

The present application claims priority to U.S. Provisional Application Ser. No. 61/884,419 filed Sep. 30, 2013, the contents of which are hereby incorporated by reference in their entirety.

TECHNICAL FIELD

The present application relates to the field of optical coherence tomography, in particular to improvements in functional optical coherence tomography techniques such as OCT angiography and Doppler optical coherence tomography.

BACKGROUND

Functional Optical coherence tomography (OCT) extensions provide additional contrast that partially mitigate the missing specificity of OCT. Doppler OCT and OCT angiography are among the functional modalities that are closest to their clinical translation. The latter provides microvascular contrast without the need of dye administration, thus allowing for screening and frequent treatment monitoring. The principle is based on observing signal decorrelation or motion contrast due to moving red blood cells within vessels. There exist a multitude of methods to extract this decorrelation signature. The easiest method to be used with swept source OCT is based on speckle decorrelation [16]. All methods have in common, that dense sampling is needed to achieve good vascular contrast. The highest sensitivity is achieved when signal decorrelation between successive tomograms is assessed. Taking several tomograms at the same location however comes at the price of measurement time, which should be kept short for retinal imaging. Otherwise motion artifacts cause degradation of contrast and resolution.

Phase-resolved Doppler optical coherence tomography (PR-D-OCT) is a non-invasive imaging technique that provides depth-resolved quantitative knowledge about motion with high resolution and at high speed [1]. Applied to functional tissue imaging, the blood velocity of selected vessels can be determined together with their cross sectional diameter, which permits calculation of the volumetric blood flow. Knowledge of tissue perfusion provides valuable information about tissue health or treatment progression. PR-D-OCT is however only sensitive to the projection of the velocity along the illumination beam, and therefore requires knowledge of the Doppler angle, a, between vessel orientation and optical axis, to obtain the absolute velocity. At this point it should be mentioned that apart from PR-D-OCT also other methods exist to determine the axial flow velocity component or in general the velocity component in direction of illumination and detection such as resonant Doppler OCT [26], or joint time frequency domain OCT [25]. All methods that measure the axial velocity component share the same disadvantage of missing knowledge about the Doppler angle.

Several absolute velocity methods have been developed in an attempt to address this issue. First approaches employed the tomographic information readily available with OCT to determine $\alpha$ [2-4]. While being a valid approach for rather steep vessels, an accurate evaluation of the velocity becomes challenging in vascular plexuses close to perpendicular to the optical axis because of the precision required on $\alpha$. Recently, a method demonstrated a direct calculation of the blood flow from en face cross sections [5]. It advantageously uses the fact that the dependence of the velocity and vessel cross section in the en face plane on $\cos(\alpha)$ cancels each other for the flow calculation. Again, an accurate value is only obtained for steep vessels like the one present in the optic nerve head (ONH) of the human eye [6-8]. Other methods rely on the determination of the 3D velocity vector by measuring the same sample point under different angles with several beams and corresponding detection channels with detailed knowledge of the probing beam geometry. Dual-beam bidirectional OCT [9] employs two different directions and allows the determination of the absolute velocity by knowledge of $\beta$, the angle between illumination plane and vessel orientation in the en face plane. This technique is particularly suitable for posterior pole blood flow assessment. Indeed, multi-beam methods rely on the exact superposition of beams, a condition that becomes critical to fulfill with increasing number of beams and the limited optical quality of the eye. The flow is later calculated by multiplying the absolute velocity with the vessel cross section, usually obtained from a separate fundus camera [10]. Acquisitions with large $\beta$ require high precision knowledge of its value. Moreover, the method ultimately fails for $\beta$ reaching 90°. We previously demonstrated an extension of the method's flexibility by rotating the illumination plane with a Dove prism to an angle parallel to the vessel orientation [11]. Under such condition, the sensitivity of the velocity calculation on $\beta$ is low. Still, for more complex vascular structures this condition cannot be met for every vessel at the same time. Also, because of patient motion, the scanning trajectory can deviate from the ideal and expected position. To account for $\beta$ would therefore require a live fundus camera or a registration algorithm [12].

SUMMARY

Here we present methods to improve functional optical coherence tomography techniques by analyzing imaging data collected at multiple angles relative to the sample. The proposed multi beam system and methods are capable to assess both depth resolved vascular structure and quantitative blood flow. In one embodiment, we describe how to calculate directly the absolute velocity and blood flow from bidirectional OCT tomograms independent of angle, that is without knowledge of the Doppler angle, $\alpha$, or the en face angle, $\beta$. The approach is particularly apt for vessels with large Doppler angles $\alpha$, where the method based on en face cross sections fails. In another embodiment we describe a method to improve the contrast of OCT angiography images. Illuminating the sample at different angles results in distinct speckle patterns that are averaged on summation of both channels thus improving contrast in the image. The basic embodiment involves two beams that are incident upon the sample from two distinct directions, but more than two beams could be utilized as well. The techniques could apply to different types of OCT systems including but not limited to swept-source OCT and spectral-domain OCT.

BRIEF DESCRIPTION OF FIGURES

The patent or application file contains at least one drawing executed in color. Copies of this patent or patent application publication with color drawing(s) will be provided by the Office upon request and payment of the necessary fee.

FIG. 2(a) shows the disk containing two slits on opposite sides. FIG. 2(b) shows how trigger pulses that are generated per optical rotation of the beams are used to synchronize the galvo scanners (GALVO) with the rotation in the case of circumpapillary scans. FIG. 2(c) shows an en face image of the optic nerve head of an eye with a circumpapillary scan pattern and the location of the two channels for each rotation.

FIG. 4 shows flow charts outlining the steps involved with two embodiments of the present application related to calculating the flow of a vessel through a cross-section using bidirectional OCT data. FIG. 4(a) shows the steps in a basic embodiment while FIG. 4(b) shows a specific approach to calculating angle independent flow.

FIG. 5 illustrates the results for In vitro validation of the technique with a perfused capillary. Circle, square and diamond markers indicate the measured velocity, the corrected velocity according to the cosine of the varied angle and the measured flow respectively. The dashed lines indicate the set velocities and flow as well as the theoretical reduction of the velocity. FIG. 5(a) shows the variation of β for α≈0°. The cross sections are plotted for β=0, 30 and 60°. FIG. 5(b) shows the variation of α for β≈0 and β≈50° in black and gray respectively. For better visibility the flow was set slightly different.

FIG. 6 illustrates the results of In vivo validation of the technique on a retinal artery of a healthy volunteer. FIG. 6(a) shows ~5° field of view OCT en face view indicating the measurement area ~7° inferior to the ONH. B-scan time series of ~3° (white lines) were acquired at different y locations crossing the artery with different β. FIG. 6(b) shows the result of the quantitative evaluation of the different locations, 1 to 8 from left to right. The flow (cross marker) remains constant with a relative standard deviation (RSD) of ~3%. The measured velocity (circle marker) is reduced for larger β. With known β the absolute velocity can be determined (+marker).

FIG. 8 shows the result of the OCT angiography embodiment for contrasting the parafoveal capillary network of a healthy volunteer. FIG. 8(a) shows a tomogram or B-scan of a sample. The data is broken into three slabs as indicated by boxes 801-803. FIGS. 8(b), 8(c) and 8(d) show the resulting angiography en face projections for the different slabs of data in FIG. 8(a) with box 801 shown in FIG. 8(b), box 802 shown in FIG. 8(c), and box 803 shown in FIG. 8(d). For each slab two angiography enface projections are presented. The images on the left hand sides were created from a single volume, while the ones on the right hand sides were created by angular compounding by using an additional volume acquired under a different angle.

DETAILED DESCRIPTION

Figure 1:
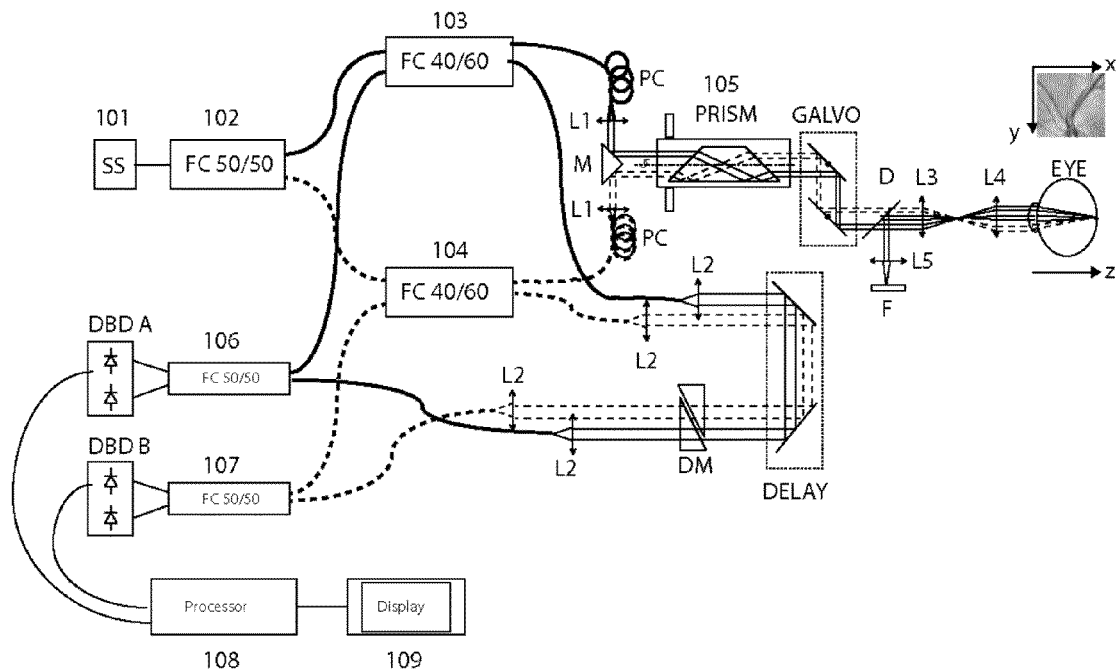
FIG. 1 is a schematic of an optical setup that can be used to perform the technique described herein.
Figure 2:
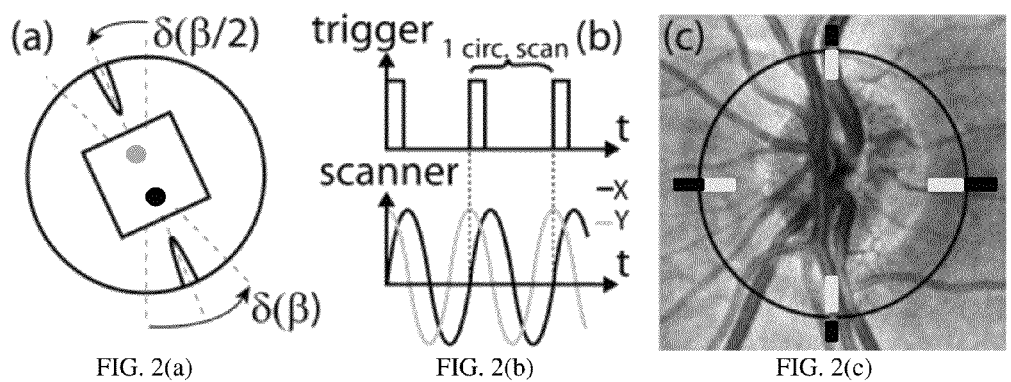
FIG. 2 illustrates the operation of the phase spinning disk used in the optical set-up illustrated in FIG. 1.

The optical setup of a rotating dual-beam bidirectional OCT system that can be used to collect and process the data according to the methods of the present application is shown in FIG. 1 and also described in reference 11 hereby incorporated by reference. While the system description is focused on an SS-OCT embodiment, any OCT capable of collecting multi-directional OCT data such as a spectral domain OCT system, could also be employed. The light source (101) in FIG. 1 is a swept source, centered at 1050 nm. In a preferred embodiment, the source has an optical bandwidth of 110 nm with an axial resolution in tissue of 5 µm. A separate fiber-based interferometer is used for both illumination directions, detected in channels A and B. A first fiber coupler (102) separates the beam of light from the light source into two individual interferometers, one for each beam (channel) A and B in solid and dashed lines respectively. The light in both interferometers is split into reference and sample arms by fiber couplers (103) and (104). In the sample arms, the polarization state of the light in each of the interferometers can be adjusted by polarization controllers (PC). The light from both interferometers is collimated using lenses (L1). The two beams are then aligned parallel to the optical axis with a defined lateral separation by reflection on a coated right angle prism (M). Displacement of that prism allows for varying the beam separation. Both beams are then transmitted through a Dove prism (PRISM). The Dove prism is employed to rotate the illumination plane. The Dove prism can freely rotate around its longitudinal central axis that is aligned with the optical axis. The beams have equal distance to the rotation axis. The continuous rotation is driven by a DC motor in open-loop (not shown). The Dove prism has the property to optically rotate an image twice when it mechanically rotates once. For synchronization of the rotation with the OCT system, a disk with two opposite slits is mounted on the rotation stage (105). The disk blocks the beam of a light, while the slits let the beam pass as illustrated in more detail in FIG. 2. As soon as the beam is able to pass, the light barrier circuitry generates a trigger pulse. Since the disk contains two slits on opposite sides (see FIG. 2(a)), one trigger pulse is generated per optical rotation of the beams. This signal is in particular needed to synchronize the galvo scanners (GALVO) with the rotation in the case of circumpapillary scans (see FIG. 2(b)). In case one chooses to acquire circumpapillary scans, the phase between the rotation and the circular scan can be adjusted such as to obtain a small 46 for radial vessels exiting the ONH (see FIG. 2(c)). Instead of using the described slit disk in combination with the light barrier circuitry to generate trigger signals for synchronization as described above, one could also use a motor with position control. The motor position control would provide information about the dove prism's rotation state, which can be used for synchronization with the galvo scanners. If only vessels with a common orientation are measured, the rotation of the dove prism can also be stopped to fix the orientation of the illumination plane. If only vessels with two or a small number of predominant orientations are measured, like for example in the macula, continuous rotation of the two beams is not necessary. Instead one could simply create a switch, which allows switching the illumination geometry between distinct orientation states. Such a switch could be implemented by a motorized rotation system as described above or for example with a rotatable mirror which directs the two beams through distinct sample paths according to its orientation, each containing a dove prism with a distinct fixed orientation.

The galvo scanners (GALVO) are used to steer the beam across a series of transverse locations on the sample, in this case an eye (EYE). On the scan mirrors the two beams are placed symmetrical around their pivot points. Lenses (L3) and (L4) form a telescope, which allows telecentric scanning of the retina of the eye. The beam separation in the pupil of the eye and beam size are determined by the scanning mirror aperture and the telescope's (L3,L4) angular magnification. In this experimental set-up of FIG. 1, the angular magnification is 1.5× and the theoretical spot size on the retina is ~25 µm. Fixation screen (F) provides a fixation target for the eye to focus on during examination. The light in the sample arm for both channels is then backscattered by the sample (in this embodiment the retina) and travels back to the individual collimation lenses L1, where it is coupled back into the single mode fiber of the respective interferometers. In the reference arm, both beams pass through lenses (L2) and travel the same delay line (DELAY). Dispersive elements (DM) in the reference arm can be used to match or offset the dispersion between reference and sample arm. At the fiber couplers (106) and (107), reference and sample light is combined and coherently interferes. The combined light is detected with dual-balanced detectors (DBD A) and (DBD B).

The output from the detectors (DBD A and DBD B) is digitized with an analog-to-digital converter and supplied to a processor (108). The processor generates OCT signal output from the detector signals and can generate images of the sample based on the digitized signals. The results can be stored in the processor or displayed on a display (109). The processing and storing functions may be localized within the OCT instrument or functions may be performed on an external processing unit to which the collected data is transferred. This unit could be dedicated to data processing or perform other tasks which are quite general and not dedicated to the OCT device. The sample and reference arms in the interferometer could consist of bulk-optics, photonic integrated circuits (PIC), fiber-optics or hybrid bulk-optic systems and could have different architectures such as Michelson, Mach-Zehnder or common-path based designs as would be known by those skilled in the art.

The interference causes the intensity of the interfered light to vary across the spectrum. In Fourier Domain optical coherence tomography (FD-OCT), each measurement is the real-valued spectral interferogram ($S_j(k)$). The real-valued spectral data typically goes through several postprocessing steps including background subtraction, dispersion correction, etc. The Fourier transform of the processed interferogram, results in a complex valued OCT signal output $A_j(z)=|A_j|e^{i\phi}$. The absolute value of this complex OCT signal, $|A_j|$, reveals the profile of scattering intensities at different path lengths, and therefore scattering as a function of depth (z-direction) in the sample. Similarly, the phase, $\phi_j$ can also be extracted from the complex valued OCT signal.

The profile of scattering as a function of depth is called an axial scan (A-scan). A set of A-scans measured at neighboring locations in the sample produces a cross-sectional image (tomogram or B-scan) of the sample. A collection of B-scans collected at different transverse locations on the sample makes up a data volume or cube. For a particular volume of data, the term fast axis refers to the scan direction along a single B-scan whereas slow axis refers to the axis along which multiple B-scans are collected. A variety of ways to create B-scans are known to those skilled in the art including but not limited to along the horizontal or x-direction, along the vertical or y-direction, along the diagonal of x and y, or in a circular or spiral pattern. The invention would apply equally to any cross sectional image covering a range of transverse locations on the sample.

A set of B-scans collected at the same or closely spaced locations on the tissue are used in motion contrast techniques. One such scanning protocol is MB scanning where a series of A-scans are collected along an axis to generate a B-scan. The scanning is repeated at the same or densely spaced locations over time. Generating motion contrast information refers to comparing consecutive tomograms or B-scans from approximately the same location to isolate changes due to motion in the sample. The time difference between consecutive B-scans depends on the system speed (A-line rate), number of A-scans in a single B-scan and the time it takes to return to the start position (fly-back times).

Figure 3:
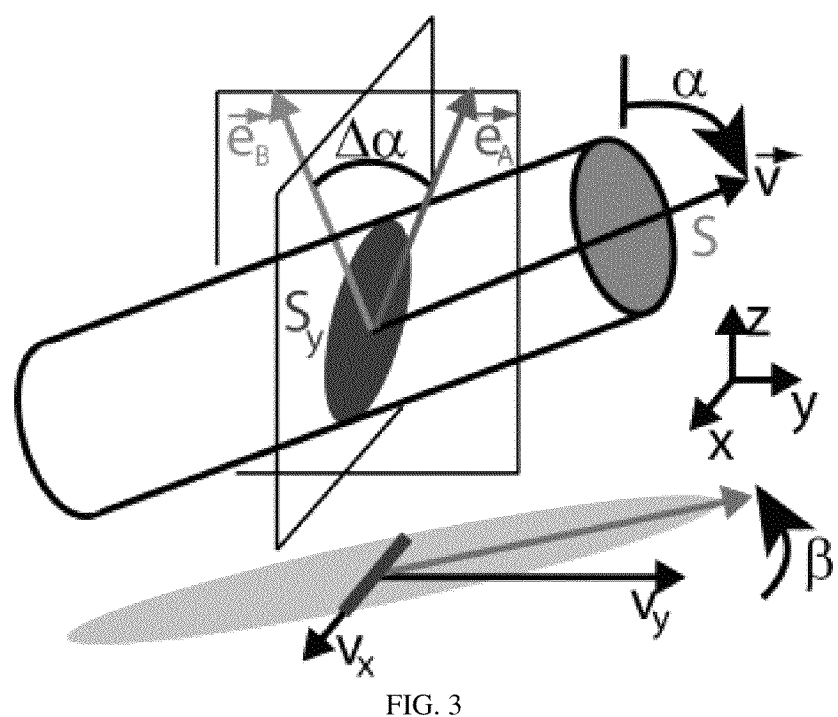
FIG. 3. Illustrates the coordinates of the vessel and illumination plane (y-z plane, spanned by vectors $\vec{e}_A$ and $\vec{e}_B$) relative to the scanning (x,y) and optical (z) axes of a bidirectional Doppler system.

FIG. 3 introduces the system of coordinates for the PR-D-OCT embodiment of the present application indicating Doppler angle, $\alpha$, and en face angle, $\beta$ for a particular velocity vector, $\vec{v}$ having a cross-section, S. The basis of coordinates (x,y,z) is given respectively by the raster scanning, fast (x-axis) and slow axis (y-axis) directions, and the optical (z) axis, which is the resulting vector of the illumination direction unit vectors $\vec{e}_A$ and $\vec{e}_B$. The velocity of the flow in this coordinate system is given by:

$$\vec{v}(x, y, z) = \begin{pmatrix} v_x \\ v_y \\ v_z \end{pmatrix} = v \begin{pmatrix} -\sin\beta\sin\alpha \\ \cos\beta\sin\alpha \\ \cos\alpha \end{pmatrix}. \quad (1)$$

The illumination plane is taken to be the y-z plane and is spanned by the illumination direction unit vectors that are angularly separated by $\Delta\alpha$ having the following representations:

$$\vec{e}_A = \begin{pmatrix} 0 \\ \sin\frac{\Delta\alpha}{2} \\ \cos\frac{\Delta\alpha}{2} \end{pmatrix}, \quad \vec{e}_B = \begin{pmatrix} 0 \\ -\sin\frac{\Delta\alpha}{2} \\ \cos\frac{\Delta\alpha}{2} \end{pmatrix}. \quad (2)$$

The velocity measured in both channels is given by the projection $v_A$ and $v_B$ of $\vec{v}$ along the respective illumination direction:

$$v_A = \langle \vec{v}, \vec{e}_A \rangle = v_y \sin\frac{\Delta\alpha}{2} + v_z \cos\frac{\Delta\alpha}{2}, \quad (3)$$

$$v_B = \langle \vec{v}, \vec{e}_B \rangle = -v_y \sin\frac{\Delta\alpha}{2} + v_z \cos\frac{\Delta\alpha}{2}, \quad (4)$$

where in the case of PR-D-OCT, the velocity is derived for each channel A and B from the respective phase difference between A-scans $\Delta\phi_{A,B}$ according to:

$$v_{A,B} = \frac{\Delta\varphi_{A,B}}{2knT}, \quad (5)$$

with k, the central wavenumber, n, the refractive index of blood and T, the measurement time between phase measurements Taking the difference of the velocity between both channels cancels the axial velocity component, $v_z$, and thereby the dependency on the Doppler angle $\alpha$:

$$\Delta v = v_A - v_B = 2v_y \sin\frac{\Delta\alpha}{2} \cong v_y \Delta\alpha, \quad (6)$$

assuming a small angular separation Δα between both beams. We observe the dependence of the measured velocity difference on the velocity y-component, i.e., in the direction orthogonal to the fast scanning or tomogram direction. The absolute velocity can then be derived according to (1):

$$v = \frac{v_y}{\cos\beta\sin\alpha} \cong \frac{\Delta v}{\Delta\alpha\cos\beta\sin\alpha}. \tag{7}$$

In standard bidirectional PR-D-OCT, the en face angle, β, is obtained from a fundus view, and the Doppler angle is large)(α≈90°. Under this condition, Eqn. (7) becomes independent of α [9,13]. This assumption is usually accurate for retinal vessels outside the ONH region. Maintaining small β makes it possible to retain accuracy on the absolute velocity without precise knowledge of β. However for increasing β, or in the presence of tortuous vessels, this method becomes inaccurate.

Here, we calculate directly the flow, F, by selecting an appropriate cross section (S) orientation:

$$F = \int_S \vec{v}\cdot\vec{n}dS = \int_{xz} \vec{v}\cdot\vec{e}_y dS = \int_{xz} v_y dS, \tag{8}$$

With, $\vec{n}$, the normal to the cross section. By using Eqn. (6) in Eqn. (8), we get:

$$F = \frac{1}{\Delta\alpha}\int_{xz} \Delta v dS = \frac{\overline{\Delta v}}{\Delta\alpha}S, \tag{9}$$

with S, the vessel cross section scaling as 1/(sin(α)cos(β)). This expression is independent of α and β and therefore does not require reading β from a fundus view or rely on any assumption on α. The dependence on the angles of the measured absolute velocity and the vessel cross section cancels each other by orientating the illumination plane along y and evaluating the flow in (x,z) tomograms. Practically, the mean velocity is calculated for each channel independently over pixels within the respective blood vessel cross sections, the mean velocities are subtracted and divided by the angle between the illumination beams, and then multiplied with the mean cross section according to:

$$f = \frac{\overline{v_A} - \overline{v_B}}{\Delta\alpha}\sum_{xz} \Delta S \approx \frac{\overline{v_A} - \overline{v_B}}{2\Delta\alpha}(S_A + S_B), \tag{10}$$

with ΔS the pixel size, and $S_{A,B}$ the cross section in each channel. The vessel cross-sections $S_{A,B}$ can be manually segmented within the intensity and/or phase B-scans or automatically by vessel segmentation algorithms as for example described by Wehbe et al. [27],Singh et al. [28], or Pilch et al. [29]. Calculation of the flow from phase difference tomograms cancels the dependence of absolute velocity and vessel cross section on the vessel angles. Limitations of this approach regarding the angular range of β are discussed later in the context of the experimental validation.

In case α is close to 90 degrees, one can use an alternative calculation of the flow according to:

$$F = \frac{1}{\Delta\alpha}\left[\sum_{xz} v_A \Delta S - \sum_{xz} v_B \Delta S\right], \tag{11}$$

where the sums are taken over the cross sections in the respective channels. ΔS is calculated laterally (Δx) according to the number of A-scans over the scanning range, which for eye posterior pole imaging requires knowledge of the eye length. The axial extension (Δz) is obtained from the geometrically scaled OCT tomogram, assuming a group refractive index in tissue of 1.34.

Again it should be mentioned that the presented principle applies to any Doppler OCT method that is capable of measuring the axial velocity component in the direction of the illumination and detection, such as resonant Doppler OCT [26], or Joint Time Frequency OCT [25]. PR-D-OCT is just one example. In case the illumination and detection directions do not coincide, the measured axial velocity component will be along the direction of the vector sum of illumination and detection direction.

FIG. 4(a) outlines the general steps of the angle dependent flow calculation of the most basic embodiment. OCT data sets suitable for Doppler analysis are acquired for each angle (channel) in steps 401 and 402. The data can be acquired sequentially or simultaneously. Each data set should contain one or more measurements made at approximately the same transverse location on the sample. Next, the OCT data is processed and the axial velocity components are determined. In the case of PR-D-OCT the axial velocity components are proportional to the phase differences between the measurements taken at approximately the same location in each data set (steps 403 and 404). From these velocity components, the flow within each vessel for a particular vessel cross section is determined independent of the Doppler and en face angles (Step 405). The results of this calculation are then displayed or stored. FIG. 4(b) shows a more specific embodiment. The data is collected and axial velocity differences are calculated the same as in FIG. 4(a) (Steps 401-404). The further steps of FIG. 4(b) illustrate one specific angle independent measurement technique. The mean velocity for each data set is calculated according to Eqn. (5) in steps 407 and 408. The mean axial velocities for the two data sets are subtracted to determine the flow according to either Eqn. (9), (10), or (11) in step 409. The flow can then be displayed or stored (step 410). A key aspect of both embodiments is that the flow within the sample can be calculated without using the Doppler (α) and en face (β) angles.

The specific PR-D-OCT method described herein has been validated experimentally both in vitro and in vivo. We will first describe the in vitro verification. The flow phantom is a capillary of 300 μm diameter, perfused by a solution of one third of milk and two thirds of water at constant flow set by a syringe pump. The capillary is placed in the focal plane of a 30 mm focal length lens and is mounted on a stage allowing for both tilt and rotation. The capillary was immersed in water for reducing refraction at its outer surface. We acquire B-scan time series along the fast axis over 3 degrees. A series in this case is composed of 60 B-scans, each consisting of 3250 A-scans. The number of A-scans per B-Scans has been chosen to be the maximum as allowed by the current acquisition configuration but other scan configurations can be envisioned by one skilled in the art. Dense sampling reduces phase noise and offers the flexibility for enhanced velocity dynamics analysis [11]. The mean phase difference value is calculated for each channel by averaging the phase difference between successive A-scans over the $m_{A,B}$ pixels of the capillary open cross section that have a higher intensity than a manually fixed threshold, according to [14]:

$$\overline{v}_{A,B} = \frac{1}{2knT} \angle \left( \sum_{m_{A,B}} e^{i\Delta\phi_{A,B}(m)} \right).$$  (12)

The flow is calculated according to Eqn. (10) over the same pixel set, where ∠(.) denotes the argument of a complex number.

FIG. 5 shows the result of the in vitro experiment with a perfused capillary collected using the experimental set-up illustrated in FIG. 1. The circle and diamond markers indicate the measured velocity values averaged over the time series. If not indicated, their size denotes the corresponding standard deviation. The dashed-dotted lines represent the set values for velocity and flow. The square marker values were obtained by correcting the measured velocity according to the known set angle (Eqn. (7)). We first varied β from 0 to 70° by keeping α≈0° (see FIG. 5(a)). For angles larger than 70°, the capillary cross section doesn't fit into the imaging lateral range and the difference between both channels becomes closer to the phase noise level. It is important to note that the flow can be measured accurately for β larger than 45°, meaning that two acquisitions with a 90° shift of the illumination plane by Dove prism flipping is sufficient to assess all vessels. In a second experiment, we varied α by keeping β≈0° and β≈50° (respectively in black and gray in FIG. 5(b)). The angle range was selected to encompass the typical angle dynamics of horizontal plexuses. The flow was slightly different for both angles β, and set such that the measured phase difference does not exhibit phase wrapping artifacts. Again, the flow is independent of the vessel's angle. Variations around the set values are attributed to the pump.

For in vivo testing of the technique, we measured the blood flow in the retina of a healthy volunteer. An artery showing various β in the fundus view over a constant segment was selected. Its blood velocity and flow were successively assessed at different y positions. FIG. 6(a) shows an OCT en face image of an approximately five degree field of view of the measurement area located at ~7° inferior to the optic nerve head (ONH) of a human eye. The location of measurement was set by adjusting the fixation target while monitoring the on-line display of the OCT en face projection during continuous raster scanning. The different B-scan positions, denoted by white lines in FIG. 6(a), were assessed by modifying the DC offset of the slow axis scanner driving voltage. The measurement protocol at a single location was previously described in detail [11]. B-scan time series are acquired at 24 Hz, each tomogram of each channel consisting of 3250 A-scans, spanning over 3°. The phase difference data for each channel is first processed separately. A bulk motion algorithm based on histogram analysis can be used to correct for phase fluctuations [15]. The vessel cross section was manually segmented for both beams in parallel assuming elliptic shapes. The constant size of the ellipse is determined at the systolic pulse phase. The mean velocity and flow are calculated over the segmented vessel cross sections for each channel. Subsequently the values are combined according to Eqn. (7) and Eqn. (10) to obtain the absolute velocity and flow values. The subject's eye length of 23.5 mm, as measured with an IOL Master (ZEISS), can be used to scale the vessel areas and Δα(3.9°).

FIG. 6(b) presents the results of the quantitative evaluation of the different B-scan locations (B-scans 1-8 in FIG. 6(a) are shown from left to right in FIG. 6(b)). The values of mean velocity and flow are averaged over one cardiac cycle. The blood flow (cross markers) remains constant with a relative standard deviation (RSD) of ~3%. In contrary, the measured velocity (circle markers) shows smaller values when the vessel is not oriented along the illumination plane as expected from Eqn. (7). With known β, the absolute velocity can be determined (+marker). The β-corrected velocities displayed in FIG. 6(b) do not account for variation of the Doppler angle α, which might explain the residual deviation from a constant velocity value.

The results indicate that the flow calculation is accurate and indeed independent of the vessel orientation. However, there are practical limitations to the angle independent flow quantification regarding its precision: the cross sectional area grows with increasing angle β (see FIG. 5(a)) and the phase difference tends to the phase noise limit given by the signal-to-noise ratio (SNR). For large angles, β, the integral in Eqn. (10) is increasingly dominated by noise reducing the precision. Ultimately, the cross section tends to infinity as β approaches 90°. For small Doppler angle, α, on the other hand, the measured phase difference tends also to the noise level as expected from Eqn. (7), which as well limits the precision of the method in this range. To achieve higher precision for flow quantification at smaller Doppler angles the en face method with a single beam becomes the alternative [5]. As it is based on en face sections from full volumes, it requires, in contrary to our B-scan based method, rapid scanning or a proper synchronization to the cardiac cycle [7], and a fast acquisition system.

Currently, phase wrapping limits the velocity dynamic range. This sets, for a given velocity, a lower boundary to a for which the mean velocity can be accurately measured. Nevertheless, advanced unwrapping algorithms could solve this current limitation. The phase noise level in general sets a lower limit to the Doppler velocity dynamic range. It can be extended by calculating the phase difference over longer time or respective A-scan intervals [11].

The presented flow calculation further improves the flexibility of the bidirectional configuration. It removes the need for registration algorithms that extract β by locating the tomogram in the fundus view. All large retinal vessels can be assessed with a single circular scan pattern with a synchronous rotation of the Dove prism [11]. In that case, the illumination is locally perpendicular to the scanning direction and therefore allows for a direct flow calculation even if vessels deviate from the β≈0° condition. It makes the bidirectional method a viable solution to clinical applications. A critical requirement for accurate ophthalmic flow measurement with this technique remains the proper overlapping of both beams on the retina.

The accuracy for flow assessment is fully angle independent as opposed to standard bidirectional PR-D-OCT [11]. The angular range for β is simply limited by phase noise and SNR. This restriction on the precision could be circumvented by taking two acquisitions with a 90° rotation of the illumination plane with respect to each other.

Figure 7:
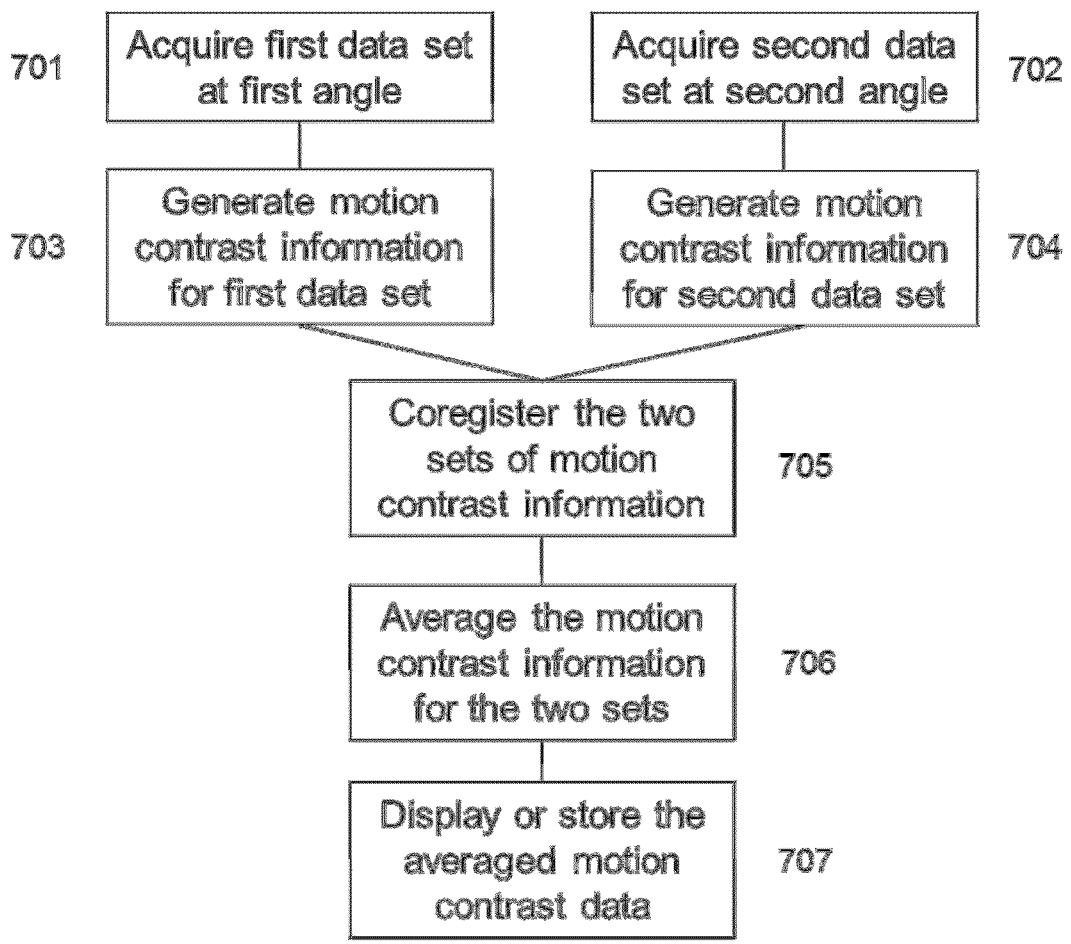
FIG. 7 shows a flow chart outlining the steps involved with one embodiment of the present application related to generating improved OCT angiography images using bidirectional OCT data.

In addition to the advantages to quantitative functional measurements like Doppler discussed above, the bidirectional OCT data can also have advantages in visualization of motion contrast or OCT angiography. A flow chart of an exemplary embodiment where bidirectional OCT data is used to generate improved OCT angiography images is illustrated in FIG. 7. OCT data sets suitable for OCT angiography analysis are acquired for each angle (channel) in steps 701 and 702. The data can be acquired sequentially or simultaneously. Each data set should contain one or more measurements made at approximately the same transverse location on the sample. Next, any one of a number of motion contrast algorithms are applied to the OCT data set in steps 703 and 704 to quantify the changes between the measurements taken at the approximately same location. Motion contrast information is typically displayed as an en face image in which three dimensional data has been reduced to two-dimensions by summing, integrating or otherwise assigning a single representative value to a specific range of axial values for each transverse location. Once the motion contrast information is generated for each channel, the data between the two channels are coregistered (step 705) and the values are averaged for the two channels (step 706) to generate a single motion contrast data set (step 707). The averaged motion contrast data is then displayed, typically as an en face image, or stored for further processing.

The OCT angiography images presented in FIG. 8 were collected with the experimental set-up illustrated in FIG. 1. An 8 degree field of view image was acquired at 200 KHz at the fovea region and optic nerve of a subject's eye with two beams each having a different angle relative to the sample. The speed can be further enhanced to 400 kHz by splitting the spectra into two halves in post-processing, each sampling a different lateral location (see for example US Publication No. 2013/0301000 hereby incorporated by reference). The total acquisition time is about 5 sec. The X-scanner scans linearly whereas the Y-scanner scans in steps with a vertical sampling of 400 points. In the examples presented herein, we recorded 4 tomograms at each or close to each sampling point in the y direction resulting in a total of 1600 tomograms per volume respectively. The motion contrast or OCT angiography information can be obtained by calculating variances within the data set, in this case between successive B-scans taken at each of two different angles relative to the sample. The motion contrast technique can be applied to the real part of the processed OCT signal (intensity), the imaginary part of the complex OCT data (phase), or a combination of the two. The B-scans can be logarithmically scaled prior to subtraction as is well known by those skilled in the art. References 19-25 hereby incorporated by reference describe a range of techniques capable of resolving motion contrast information including techniques based on taking differences between measurements and calculating variance within the data. For the images displayed in FIG. 8, a speckle variance approach was used. [17] The resulting OCT angiography images from each beam are then averaged for tomograms taken at the same vertical position. The difference tomograms exhibit strong contrast for moving structures whereas static structures are ideally suppressed [16-17].

Having two channels available with distinct illumination directions allows for combining the two OCT angiography images and achieving speckle reduction though angular compounding. To accomplish this, we divided the depth coordinate of the motion contrast volume into distinct axial sections, and summed over the enface planes to produce axial projections. The fundus projections of both angular channels can then be coregistered as is known in the art, in the examples presented herein the UnwarpJ plugin of ImageJ was used [18]. UnwarpJ constructs a transformation Matrix, which transform one image elastic and consistent to the reference image. After transformation the co-registered en-face projections are averaged which increases contrast within the image. The 3D motion contrast stack was axially registered and flattened to the RPE prior to calculating the axial projections. In addition one could apply a binary mask to the angiography tomograms that is taken from the thresholded intensity tomograms for excluding noise areas without signal.

FIG. 8 shows the result of the OCT angiography embodiment for contrasting the parafoveal capillary network of a healthy volunteer. We used three slabs as indicated by boxes 801-803. The boxes in the representative tomogram (FIG. 8(a)) are the slabs over which the respective en-face angiographic projections are calculated. The nerve fiber and ganglion cell layer network slab is indicated by box 801, the capillary bed at the inner plexiform-inner nuclear layer boundary slab is indicated by box 802 and the third slab at the inner nuclear and outer plexiform layer is indicated by box 803 (see FIG. 8(a)). FIG. 8(b-c) show the resulting angiography enface projections with box 801 shown in FIG. 8(b), box 802 shown in FIG. 8(c), and box 803 shown in FIG. 8(d). For each slab two angiography enface projections are presented. The ones on the left hand sides were created from a single volume, while the ones on the right hand sides were created by angular compounding by using an additional volume acquired under a different angle.

As seen from the images in FIG. 8 the contrast has been dramatically enhanced. The contrast enhancement can be further used for increasing the field of view while maintaining proper vascular details. To illustrate this, we imaged the optic nerve head with an angular extent of 16 degrees, using the same number of samples as for the 8 degree image patch. The resulting angular compounded angiography map is shown in FIG. 9(b). FIG. 9(a) is again showing the single beam result for comparison. These volumes were not axially registered and therefore exhibit line artifacts as well as missing structure on the left side of the angiography maps.

The following references are hereby incorporated by reference:

Patent Literature

US Publication No. 2013/0301000
U.S. Pat. No. 8,433,393

Non Patent Literature

1. R. A. Leitgeb, "Current technologies for high speed and functional imaging with optical coherence tomography," in Advances in Imaging and Electron Physics, Volume 168: Optics of Charged Particle Analyzers, P. W. Hawkes, ed. (Elsevier, 2011), Chap. 3.
2. R. Michaely, A. H. Bachmann, M. L. Villiger, C. Blatter, T. Lasser, and R. A. Leitgeb, "Vectorial reconstruction of retinal blood flow in three dimensions measured with high resolution resonant Doppler Fourier domain optical coherence tomography," J. Biomed. Opt. 12, 041213-041217 (2007).
3. S. Makita, T. Fabritius, and Y. Yasuno, "Quantitative retinal-blood flow measurement with three-dimensional vessel geometry determination using ultrahigh-resolution Doppler optical coherence angiography," Opt. Lett. 33, 836-838 (2008).
4. Y. M. Wang, B. A. Bower, J. A. Izatt, O. Tan, and D. Huang, "Retinal blood flow measurement by circumpapillary Fourier domain Doppler optical coherence tomography," J. Biomed. Opt. 13, 064003 (2008).
5. V. J. Srinivasan, S. Sakadžić, I. Gorczynska, S. Ruvinskaya, W. C. Wu, J. G. Fujimoto, and D. A. Boas, "Quantitative cerebral blood flow with optical coherence tomography," Opt. Express 18, 2477-2494 (2010).
6. B. Baumann, B. Potsaid, M. Kraus, J. Liu, D. Huang, J. Hornegger, A. Cable, J. Duker, and J. Fujimoto, "Total retinal blood flow measurement with ultrahigh speed swept source/Fourier domain OCT," Biomed. Opt. Express 2, 1539-1552 (2011).
7. T. Schmoll, and R. A. Leitgeb, "Heart-beat-phase-coherent Doppler optical coherence tomography for measuring pulsatile ocular blood flow," J. Biophotonics 6, 275-282 (2012).
8. W. Choi, B. Baumann, J. Liu, A. Clermont, E. Feener, J. Duker, and J. Fujimoto, "Measurement of pulsatile total blood flow in the human and rat retina with ultrahigh speed spectral/Fourier domain OCT," Biomed. Opt. Express 3, 1047-1061 (2012).
9. R. M. Werkmeister, N. Dragostinoff, M. Pircher, E. Götzinger, C. K. Hitzenberger, R. A. Leitgeb, and L. Schmetterer, "Bidirectional Doppler Fourier domain optical coherence tomography for measurement of absolute flow velocities in human retinal vessels," Opt. Lett. 33, 2967-2969 (2008).
10. R. M. Werkmeister, N. Dragostinoff, S. Palkovits, R. Told, A. Boltz, R. A. Leitgeb, M. Gröschl, G. Garhöfer, L. Schmetterer, "Measurement of absolute blood flow velocity and blood flow in the human retina by dual-beam bidirectional Doppler Fourier-domain optical coherence tomography," Invest. Ophthalmol. Vis. Sci. 53, 6062-6071 (2012).
11. C. Blatter, S. Coquoz, B. Grajciar, A. Singh, M. Bonesi, R. Werkmeister, L. Schmetterer, and R. Leitgeb, "Dove prism based rotating dual beam bidirectional Doppler OCT," Biomed. Opt. Express 4, 1188-1203 (2013).
12. A. Singh, C. Kolbitsch, T. Schmoll, and R. Leitgeb, "Stable absolute flow estimation with Doppler OCT based on virtual circumpapillary scans," Biomed. Opt. Express 1, 1047-1059 (2010).
13. C. E. Riva, G. T. Feke, B. Eberli, and V. Bernary, "Bidirectional LDV system for absolute measurement of blood speed in retinal vessels," Appl. Opt. 18, 2301-2306 (1979).
14. A. Szkulmowska, M. Szkulmowski, A. Kowalczyk, and M. Wojtkowski, "Phaseresolved Doppler optical coherence tomography-limitations and improvements," Opt. Lett., 33, 1425-1427 (2008).
15. T. Schmoll, C. Kolbitsch, and R. Leitgeb, "Ultra-high-speed volumetric tomography of human retinal blood flow," Opt. Express 17, 4166-4176 (2009).
16. A. Mariampillai, B. A. Standish, E. H. Moriyama, M. Khurana, N. R. Munce, M. K. K. Leung, J. Jiang, A. Cable, B. C. Wilson, I. A. Vitkin, and V. X. D. Yang, "Speckle variance detection of microvasculature using swept-source optical coherence tomography," Opt. Lett. 33, 1530-1532 (2008).
17. C. Blatter, T. Klein, B. Grajciar, T. Schmoll, W. Wieser, R. Andre, R. Huber, and R. A. Leitgeb, "Ultrahigh-speed noninvasive widefield angiography," Journal Of Biomedical Optics 17, 070505 (2012).
18. C. Ó. Sánchez Sorzano, P. Thévenaz, M. Unser, "Elastic Registration of Biological Images Using Vector-Spline Regularization," IEEE Transactions on Biomedical Engineering, vol. 52, no. 4, pp. 652-663, April 2005.
19. An L., Qin J., and Wang R. K., "Ultrahigh sensitive optical microangiography for in vivo imaging of microcirculations within human skin tissue beds," Opt Express 18, 8220-8228 (2010).
20. Fingler J., Schwartz D., Yang C., and Fraser S. E., "Mobility and transverse flow visualization using phase variance contrast with spectral domain optical coherence tomography," OPTICS EXPRESS 15, 12636 (2007).
21. Fingler J., Zawadzki R. J., Werner J. S., Schwartz D., and Fraser S. E., "Volumetric microvascular imaging of human retina using optical coherence tomography with a novel motion contrast technique," Opt Express 17, 22190-22200 (2009).
22. Jia Y., Tan O., Tokayer J., Potsaid B., Wang Y., Liu J. J., Kraus M. F., Subhash H., Fujimoto J. G., Hornegger J., and Huang D., "Split-spectrum amplitude-decorrelation angiography with optical coherence tomography," Opt Express 20, 4710-4725 (2012).
23. Mariampillai A., Leung M. K., Jarvi M., Standish B. A., Lee K., Wilson B. C., Vitkin A, and Yang V. X., "Optimized speckle variance OCT imaging of microvasculature," Opt Lett 35, 1257-1259 (2010).
24. Mariampillai A., Standish B. A., Moriyama E. H., Khurana M., Munce N. R., Leung M. K. K., Jiang J., Cable A., Wilson B. C., Vitkin I. A., and Yang V. X. D., "Speckle variance detection of microvasculature using swept-source optical coherence tomography," Optics Letters 33, 1530 (2008).
25. Szkulmowski M., Szkulmowska A., Bajraszewski T., Kowalczyk A., and Wojtkowski M., "Flow velocity estimation using joint Spectral and Time domain Optical Coherence Tomography," Optics Express 16, 6008 (2008).
26. Bachmann A. H., Villiger M. L., Blatter C., Lasser T., and Leitgeb R. A., "Resonant Doppler flow imaging and optical vivisection of retinal blood vessels," Optics Express 15, 408 (2007).
27. Wehbe H., Ruggeri M., Jiao S., Gregori G., Puliafito C. A., and Zhao W., "Automatic retinal blood flow calculation using spectral domain optical coherence tomography," Optics Express 15, 15193 (2007).
28. Singh A. S., Schmoll T., and Leitgeb R. A., "Segmentation of Doppler optical coherence tomography signatures using a support-vector machine," Biomed Opt Express 2, 1328-1339 (2011).
29. Pilch M., Wenner Y., Strohmayr E., Preising M., Friedburg C., Meyer Zu Bexten E., Lorenz B., and Stieger K., "Automated segmentation of retinal blood vessels in spectral domain optical coherence tomography scans," Biomed Opt Express 3, 1478-1491 (2012).

It is claimed that:

1. A method for imaging and quantifying flow within a sample using an optical coherence tomography (OCT) system, said method comprising:
    acquiring a first OCT data set for a series of transverse locations on the sample, said first data set containing a plurality of measurements of the sample, wherein the first data set contains at least two measurements that were made at approximately the same transverse location, and wherein the data set is collected with a beam of radiation having a first angle relative to the sample;
    acquiring a second OCT data set for a series of transverse locations, said second data set containing a plurality of measurements of the sample, wherein the second data set contains at least two measurements that were made at approximately the same transverse location as the at least two measurements in the first data set, and wherein the data set is collected with a beam of radiation having a second angle relative to the sample, said second angle being different than said first angle;
    determining the axial flow components for the first data set from the two or more measurements made at approximately the same location in the first data set;
    determining the axial flow components for the second data set from the two or more measurements made at the same location in the second data set;
    calculating the flow within the sample based on a combination of the determined axial flow velocity components and without using the angles of the beams relative to the sample and the en face angle; and displaying or storing the results of the calculation.

2. A method as recited in claim 1, wherein the OCT system is a swept-source OCT system.

3. A method as recited in claim 1, wherein the OCT system is spectral domain OCT system.

4. A method as recited in claim 1, wherein the OCT system is a phase-resolved Doppler OCT system and the axial flow components are determined by calculating phase differences between the two or more measurements taken at approximately the same location in the two or more data sets.

5. A method for imaging and quantifying flow within a sample using an optical coherence tomography (OCT) system, said method comprising:

acquiring a first data set using the OCT system for a series of transverse locations on the sample, said first data set containing a plurality of measurements of the sample, wherein the first data set contains at least two measurements that were made at approximately the same transverse location, and wherein the data set is collected with a beam of radiation having a first angle relative to the sample;

acquiring a second data set using the OCT system for a series of transverse locations, said second data set containing a plurality of measurements of the sample, wherein the second data set contains at least two measurements that were made at approximately the same transverse location as the at least two measurements in the first data set, and wherein the data set is collected with a beam of radiation having a second angle relative to the sample, said second angle being different than said first angle;

determining axial velocity components for the first data set from the two or more measurements made at approximately the same location in the first data set;

determining axial velocity components for the second data set from the two or more measurements made at approximately the same location in the second data set;

determining a vessel cross sectional area for each beam of radiation;

calculating the mean velocity for each data set over the vessel cross sectional area for the respective beams of radiations using the determined axial velocity components;

calculating the flow by subtracting the mean velocities for each data set, multiplying by the cross sectional areas, and dividing by the angle between the beams of radiation; and storing or displaying the results of the calculation.

6. A method as recited in claim 5, wherein the OCT system is a swept source OCT system.

7. A method as recited in claim 5, wherein the OCT system is a spectral domain OCT system.

8. A method as recited in claim 5, wherein the OCT system is a phase-resolved Doppler OCT system and the axial flow components are determined by calculating phase differences between the two or more measurements taken at approximately the same location in the two or more data sets.

9. A method for imaging a sample using an optical coherence tomography (OCT) system, said method comprising:

acquiring a first data set using the OCT system for a series of transverse locations on the sample, said first data set containing a plurality of measurements of the sample, wherein the first data set contains at least two measurements that were made at approximately the same transverse location, and wherein the data set is collected with a beam of radiation having a first angle relative to the sample;

acquiring a second data set using the OCT system for a series of transverse locations, said second data set containing a plurality of measurements of the sample, wherein the second data set contains at least two measurements that were made at approximately the same transverse location as the at least two measurements in the first data set, and wherein the data set is collected with a beam of radiation having a second angle relative to the sample, said second angle being different than said first angle;

processing the first set of data to generate first motion contrast information by quantifying changes between the two or more measurements made at the approximately same transverse location;

processing the second set of data to generate second motion contrast information by quantifying changes between the two or more measurements made at the approximately same transverse location;

coregistering the first and second motion contrast information;

averaging the coregistered first and second motion contrast information;

generating image information based on the averaged result; and storing or displaying the generated image information.

10. A method as recited in claim 9, wherein the change quantification involves taking differences between the intensities of the measurements.

11. A method as recited in claim 9, wherein the change quantification involves taking differences between the phases of the measurements.

12. A method as recited in claim 9, wherein the change quantification involves taking differences between both the phases and the intensities of the measurements.

13. A method as recited in claim 9, wherein the change quantification involves calculating the variance between the two or more measurements in each data set.

14. A method as recited in claim 9, wherein the OCT system is a swept-source OCT system.

15. A method as recited in claim 9, wherein the OCT system is a spectral-domain OCT system.

* * * * *

UNITED STATES PATENT AND TRADEMARK OFFICE
CERTIFICATE OF CORRECTION

| | | |
|---|---|---|
| PATENT NO. | : 9,046,339 B2 | Page 1 of 1 |
| APPLICATION NO. | : 14/503292 | |
| DATED | : June 2, 2015 | |
| INVENTOR(S) | : Cedric Blatter et al. | |

It is certified that error appears in the above-identified patent and that said Letters Patent is hereby corrected as shown below:

Specification

In column 6, line 58-59, delete "measurements" and insert -- measurements. --, therefor.

In column 7, line 52, delete "f" and insert -- F --, therefor.

In column 10, line 32, delete "to a" and insert -- to α --, therefor.

Signed and Sealed this
Sixth Day of October, 2015

Michelle K. Lee
*Director of the United States Patent and Trademark Office*